United States Patent [19]

Minai et al.

[11] Patent Number: 4,985,590
[45] Date of Patent: Jan. 15, 1991

[54] OPTICALLY ACTIVE BENZENE DERIVATIVES AND PROCESS FOR PREPARATION THEREOF

[75] Inventors: Masayoshi Minai, Moriyama; Takayuki Higashi, Kishiwada, both of Japan

[73] Assignee: Sumitomo Chemical Company, Limited, Osaka, Japan

[21] Appl. No.: 182,461

[22] Filed: Apr. 18, 1988

[30] Foreign Application Priority Data

Apr. 21, 1987 [JP] Japan ................................. 62-99051
May 9, 1987 [JP] Japan ................................. 62-113270

[51] Int. Cl.$^5$ ............................................. C07C 69/66
[52] U.S. Cl. ..................................... 560/184; 560/188; 568/607
[58] Field of Search ................ 560/184, 188; 568/607

[56] References Cited

FOREIGN PATENT DOCUMENTS 255219A 3/1988 European Pat. Off. .
61-63633 4/1986 Japan .

OTHER PUBLICATIONS

CA 91 (13):107942y, 1979.
CA 86 (5):29806d, 1975.
CA 105 (11):97086e, 1985.
CA 76 (20):113595k, 1971.
CA 100 (26):210535n, 1983.
Chemical Abstracts, vol. 102, No. 3, Jan. 21, 1985, p. 314, Abstract No. 20235h.
Chemical Abstracts, vol. 105, No. 23, Dec. 8, 1986; p. 487, Abstract No. 207608m.
Tetrahedron, vol. 31, pp. 235–238.
Journal of Polymer Science, Part A-1, vol. 9 (1971), pp. 3671–3673.
Synthetic Communications, 15 (13), 1153–57 (1985).
Journal of Natural Products, vol. 48, No. 4, pp. 634–637 (1985) (Ojika et al).

Polym. Prepr., 24 (2), pp. 76–77 (1983) (Jones et al.).
Bulletin of the Chemical Society of Japan, 45, 2802–2809 (1972) (Okamoto et al).
J.A.C.S., 94 (6), 1973–1978 (1972) (Spanninger et al).
Mol. Cryst. Liq. Cryst., vol. 54, pp. 9–20 (1979) (Okamoto et al).

Primary Examiner—Paul J. Killos
Attorney, Agent, or Firm—Stevens, Davis, Miller & Mosher

[57] ABSTRACT

Disclosed are novel optically active benzene derivatives represented by the formula (I):

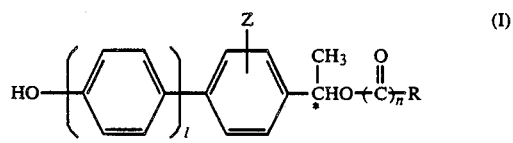

wherein R represents an alkyl or alkoxyalkyl group having 1 to 20 carbon atoms, which group may contain a halogen; Z represents a hydrogen atom or a halogen atom; l and n each represents a number of 0 or 1; and * indicates asymmetric carbon atom, and a process for preparing the above optically active benzene derivative which comprises debenzylating an optically active benzyl derivative represented by the formula (II):

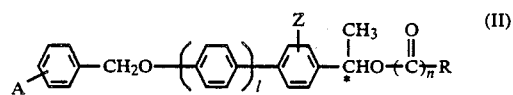

wherein, R, Z, l, n and * have the same meanings as defined above, and A represents a hydrogen atom, a lower alkyl group, a lower alkoxyl group or a halogen atom.

39 Claims, No Drawings

OPTICALLY ACTIVE BENZENE DERIVATIVES AND PROCESS FOR PREPARATION THEREOF

BACKGROUND OF THE INVENTION

1. Field of the Invention

This invention relates to the novel optically active benzene derivatives such as alkyl- or alkoxyalkyloxyethyl phenols, or -carbonyl-oxyethyl phenols, -oxyethyl-4'-hydroxy biphenyls or -carbonyl-oxyethyl-4'-hydroxy biphenyls, and a process for producing such optically active benzene derivatives.

2. Description of the Prior Art

Racemic compounds represented by the general formula

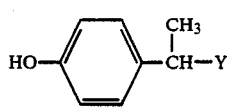

(wherein Y denotes a methoxy or ethoxy group) are disclosed in M. Ojika, J. Nat. Prod., 48 634 (1985) and J. A. Jones, Polym. Prepr., 24 76 (1983). However, the above compounds are racemic compounds and no practical use thereof is disclosed at all.

Further, the above compounds are not available as an intermediate for ferroelectric liquid crystal compounds because of being racemic compounds, whereas the compounds of the present invention can be readily derived to such ferroelectric liquid crystal compounds.

For example, as shown below, all the past prior art relied on method of introducing an optically active alkyl group into phenols, whereas the present invention relies on method wherein optically active alcohols, in which an asymmetric carbon atom is directly bonded to the benzene ring and therefore, are naturally optically active, are obtained by the asymmetric hydrolysis, and then alkylated or acylated which is followed by debenzylation to obtain optically active phenols. Thus, the present method is different from the prior art methods.

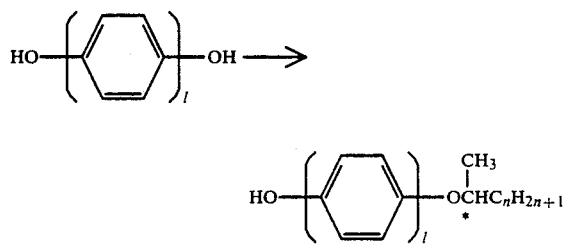

wherein l is 1 or 2 and * mark indicate asymmetric carbon atom.

SUMMARY OF THE INVENTION

In accordance with the present invention, there are provided optically active benzene derivatives represented by the formula (I):

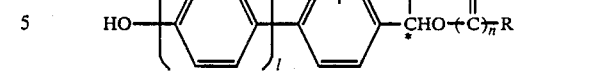

wherein R represents an alkyl or alkoxyalkyl group having 1 to 20 carbon atoms, which group may contain a halogen; Z represents a hydrogen atom or a halogen atom; l and n each represents a number of 0 or 1; and * indicates asymmetric carbon atom; and a process for preparing the same, which comprises debenzylating an optically active benzyl derivative represented by the formula (II):

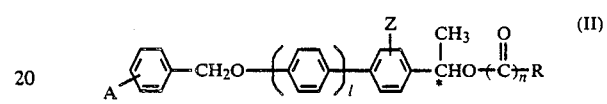

wherein R, Z, l, n and * have the same meanings as defined above, and A represents a hydrogen atom, a lower alkyl group, a lower alkoxyl group or a halogen atom;

and also a process for preparing the same which comprises reacting an optical active alcohol represented by the formula (III):

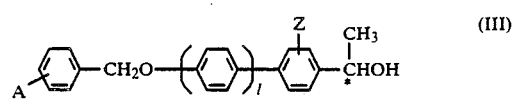

(wherein A, Z, l and * have the same meanings as defined above) with an alkylating or acylating agent represented by the formula (IV):

(wherein R is as defined above; and X represents a halogen atom, $-OSO_2R''$ or $-COY$ wherein R'' represents a lower alkyl group or a phenyl group which may be substituted with a lower alkyl group, and Y represents a halogen atom, $-OH$ or $-OCOR$) to produce an optically active benzyl derivative (II).

DETAILED DISCLOSURE OF THE INVENTION

The optically active benzene derivatives represented by the formula (I) are the novel compounds found out for the first time by the present inventors. Such derivatives, let alone their preparation process and usefulness, have been totally unknown in the art.

These optically active benzene derivatives (I) are useful as an intermediate for the preparation of pharmaceuticals, agricultural chemicals and the like. Especially significant is their availability as an intermediate for the production of organic materials for electronics, especially liquid crystal compounds. For instance, said derivatives can be led into a liquid crystal compound by reacting them with a carboxylic acid such as a benzoic acid derivative:

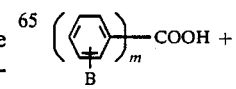

-continued

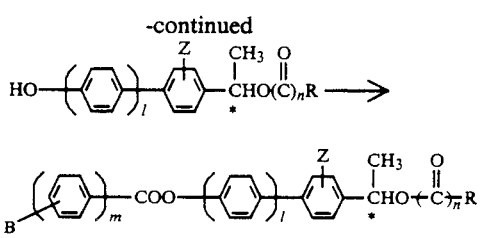

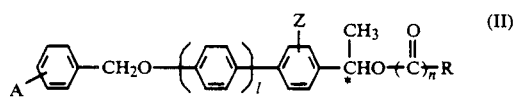

The liquid crystal compounds obtained from said optically active benzene derivatives have the very excellent properties as a ferroelectric liquid crystal material. Especially the liquid crystal compounds prepared from said benzene derivatives of the formula (I) in which substituent R contains no halogen are excellent in stability. Especially, in case of the formula (I) in which R contains no halogen and Z is hydrogen, they are excellent in stability.

Such novel and useful optically active benzene derivatives can be produced by debenzylating the optically active benzyl derivatives represented by the formula (II):

(II)

wherein R, Z, l, n and * have the same meanings as defined above, and A represents a hydrogen atom, a halogen atom, or a lower alkyl or lower alkoxyl group.

This debenzylation reaction usually comprises catalytic hydrogenation in the presence of a hydrogenation catalyst such as palladium type metal catalysts, nickel type metal catalysts such as Raney Nickel, stabilized nickel. Palladium type metal catalysts are preferably used as hydrogenation catalyst in said debenzylation reaction. Examples of such palladium type metal catalysts are palladium-carbon, palladium oxide, palladium black, palladium chloride and the like. The amount of such catalyst used in the reaction is usually in the range of 0.001 to 0.5, preferably 0.005 to 0.3 times by weight the amount of optically active benzyl derivative. The reaction is usually carried out in a solvent which is inert to the reaction, for example, water, aliphatic or aromatic hydrocarbons, alcohols, ethers, ketones, esters, and halogenated hydrocarbons, such as dioxane, tetrahydrofuran, methanol, ethanol, n-propyl alcohol, acetone, dimethylformamide, toluene, dichloromethane, ethyl acetate and the like. These solvents may be used either singly or in combination.

This reaction is carried out under normal or raised hydrogen pressure, and preferably the moment when the hydrogen absorption has reached 1 to 1.2 equivalent to the optically active benzyl derivative (II) used as starting material is set as the end point of the reaction.

The reaction temperature is in the range of $-10°$ to $100°$ C., preferably $10°$ to $60°$ C.

After the end of the reaction, the catalyst is removed from the reaction mixture by filtration or other means and the residue is concentrated or otherwise treated to obtain the desired optically active benzene derivative (I). If necessary, the product thus obtained may be purified by proper means such as recrystallization or column chromatography.

The optically active benzyl derivatives (II) used as starting material for said reaction can be produced by reacting the optically active alcohols represented by the formula (III):

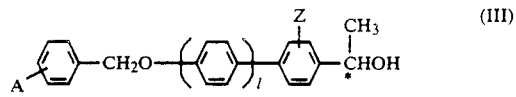

wherein A, Z, l and * represent the same as defined above with an alkylating or acylating agent represented by the formula (IV):

R—X    (IV)

wherein R is as defined above, and X represents a halogen atom, $-OSO_2R''$ or $-COY$ wherein R'' represents a lower alkyl group or a phenyl group which may be substituted with a lower alkyl group, and Y represents $-OH$, a halogen atom or $-OCOR$.

In the above reaction, in case it is desired to produce an optically active benzyl derivative of the formula (II) where n=0, an alkylating agent of the formula (IV) where X is halogen or $-SO_2R''$ is used, and in case it is desired to obtain an optically active benzyl derivative of the formula (II) where n=1, an acylating agent of the formula (IV) where X is $-COY$ is used.

The reaction using an alkylating agent is usually carried out in the presence of a basic substance. Examples of such basic substance are alkali metal hydrides such as sodium hydride and potassium hydride, alkali metal hydroxides or alkali earth metal hydroxides such as sodium hydroxide, potassium hydroxide and calcium hydroxide, alkali metal carbonates such as sodium carbonate and potassium carbonate, butyl lithium, metal alkoxides such as potassium t-butoxide, sodium methylate and sodium ethylate, metal amides such as lithium diisopropyl amide and lithium bis(trimethylsilyl)amides, and alkaline metals such as lithium, sodium and potassium.

Such basic substance needs to be used in an amount of one equivalent or more to the optically active alcohol (III). Although the upper limit is not specifically defined, the amount of said basic substance used in the above reaction is preferably in the range of one to 5 equivalents to said alcohol (III).

The alkylating agent (IV) used in this reaction is selected from the halides such as chlorides, bromides and iodides, (particularly, bromides and iodides are preferred in view of reactivity), or the sulfuric esters (methanesulfonic esters, ethanesulfonic esters, benzenesulfonic esters, toluenesulfonic esters, etc.), where necessary, these halides or sulfuric acid esters can be readily obtained by synthesis from their corresponding alcohols. These halides or sulfuric acid esters have an alkyl or alkoxyalkyl group of 1 to 20 carbon atoms which may contain a halogen, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyoctyl, propoxydecyl, butoxymethyl, butoxyethyl, butoxypropyl, butoxybutyl, butoxypentyl, butoxyhexyl, butoxyheptyl, butoxynonyl, pentyloxymethyl, pentyloxyethyl, pentyloxypropyl, pentyloxybutyl, pentyloxypentyl, pentyloxyoctyl, pentyloxydecyl, hexyloxymethyl, hexyloxyethyl, hexyloxypropyl, hexyloxybutyl, hexyloxypentyl, hexyloxyhexyl, hexyloxyoctyl, hexyloxynonyl, hexyloxydecyl, heptyloxymethyl, heptyloxyethyl, heptyloxypropyl, heptyloxypentyl, octyloxymethyl, octyloxyethyl, decyloxymethyl, decyloxyethyl, decyloxypropyl, 2-methylbutyl, 3-methylpentyl, 4-methylhexyl, 1-methylpropyl, 1-methylbutyl, 1-methylamyl, 1-methylhexyl, 1-ethylbutyl, 1-methylheptyl, 2-chloropropyl, 2-chlorobotyl, 2-bromopropyl, 2-fluoroheptyl and 2-fluorooctyl.

In case such alkyl or alkoxyalkyl group which may contain a halogen has asymmetric carbon atom, such group may be an optical active group. Among halogens, fluoro or chloro is practically more preferred. The halides or the sulfuric acid esters exemplified as above are synthesized from the corresponding monoalkylalcohols, which are, in turn, synthesized easily from the corresponding diols.

Such alkylating agent (IV) may be used in any amount not less than one equivalent to the optically active alcohol (III), but usually it is used in an amount range of one to 5 equivalents to said alcohol (III).

The solvent used in the reaction should be the one which is inert to the reaction, such as aliphatic or aromatic hydrocarbons, ethers and halogenated hydrocarbons, for example, tetrahydrofuran, ethyl ether, acetone, methyl ethyl ketone, toluene, benzene, chloroform, chlorobenzene, dichloromethane, dichloroethane, carbon tetrachloride, dimethylformamide, hexane and the like. These solvents may be used either singly or in combination, the amount thereof used in the reaction being not specified.

It is possible to use polar solvents such as dimethyl sulfoxide, hexamethyl phosphoryl amide, N-methylpyrrolidone and the like.

The reaction temperature is usually in the range of −50° to 120° C., preferably −30° to 100° C.

In case of using an acylating agent of the formula (IV) wherein X is COY, such acylating agent is selected from the aliphatic carboxylic acids such as enumerated below or the acid anhydrides or acid halides thereof: acetic acid, propionic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanic acid, isobutyric acid, 2-methylbutanoic acid, 3-methylpentanoic acid, 4-methylpentanoic acid, 2-methylhexanoic acid, 4-methylhexanoic acid, 2-methylheptanoic acid, 2-methyloctanoic acid, haloacetic acid, 2-halopropanoic acid, 2-halobutanoic acid, 2-halopropanoic acid, 2-halobutanoic acid, 2-halopentanoic acid, 3-halohexanoic acid, 2-halooctanoic acid, 2,3-dimethylbutanoic acid, 2,3,3-trimethylbutanoic acid, 2,3-dimethylpentanoic acid, 2,4-dimethylpentanoic acid, 2,3,3,4-tetramethylpentanoic acid, 2,5-dimethylhexanoic acid, 2-trihalomethylpentanoic acid, 2-trihalomethylhexanoic acid, 2-trihalomethylheptanoic acid, 3-halo-2-methylpropanoic acid, 2,3-dihalopropanoic acid, 2,3-dihalobutanoic acid, 2-halo-3-methylbutanoic acid, 2-halo-3,3-dimethylbutanoic acid, 2,5-dihalopentanoic acid, 2-halo-3-methylpentanoic acid, and 2-halo-3-monohalomethyl-4-methylpentanoic acid.

In the above examples of aliphatic carboxylic acids, "halo" refers to fluorine, chlorine, bromine or iodine, and the acid halides derived therefrom are acid chlorides, acid bromides, etc.

Such aliphatic carboxylic acids may be the optically active ones when they have asymmetric carbon atom in the molecule. Some of such optically active aliphatic carboxylic acids can be obtained by oxidizing the corresponding alcohols or by reductive deamination of amino acids. Some of them exist in nature or can be derived from optically active amino acids or oxyacids such as mentioned below which can be obtained by resolution: alanine, varine, leucine, isoleucine, phenylalanine, serine, threonine, allothreonine, homoserine, alloisoleucine, tert-leucine, 2-amino acid, norvaline, ornithine, lysine, hydroxylysine, phenylglycine, trifluoroalanine, aspartic acid, glutamic acid, lactic acid, mandelic acid, tropic acid, 3-hydroxybutyric acid, malic acid, tartaric acid, isopropylmalic acid, etc.

The reaction using such acylating agent is carried out usually in the presence of a solvent, through the presence of a solvent is not essential, with a catalyst also usually present in the reaction.

In case of using a solvent in this reaction, such solvent needs to be the one which is inert to the reaction. Examples of such solvents are aliphatic or aromatic hydrocarbons, ethers and halogenated hydrocarbons, such as tetrahydrofuran, ethyl ether, acetone, methyl ethyl ketone, toluene, benzene, chlorobenzene, dichloromethane, dichloroethane, chloroform, carbon tetrachloride, dimethylformamide, hexane and the like. These solvents may be used either singly or in combination. No particular limitation is imposed on the amount of such solvent(s) to be used in the reaction.

In case of using an acid anhydride or acid halide of an aliphatic carboxylic acid as acylating agent, it needs to be used in an amount of one equivalent or more to the optically active alcohol (III). The upper limit of its amount to be used in the reaction is not defined, but it is preferably set at 4 equivalents to said alcohol (III).

As catalyst, there can be used organic or inorganic basic substances such as dimethylaminopyridine, triethylamine, tri-n-butylamine, pyridine, picoline, lysine, imidazole, sodium carbonate, sodium methylate, potassium hydrogencarbonate and the like. Organic or inorganic acids such as toluenesulfonic acid, methanesulfonic acid, sulfonic acid, etc., are also usable as catalyst.

In use of such catalyst, when for instance an acid halide of an aliphatic carboxylic acid is used as a starting material, pyridine is best suited for use as catalyst.

The amount of the catalyst used in the reaction is not necessarily specified as it differs depending on the type of the acid anhydride or acid halide of an aliphatic carboxylic acid used and its combination with the catalyst used, but in case of using an acid halide as a starting material, the catalyst is used in an amount of one equivalent or more to said acid halide.

When an aliphatic carboxylic acid is used as acylating agent, the reaction usually comprises dehydrating-condensation which is carried out by using an aliphatic carboxylic acid in an amount of 1 to 2 equivalents to the optically active alcohol (III) in the presence of a condensing agent.

Carbodiimides such as N,N'-dicyclohexylcarbodiimide, N-cyclohexyl-N'-(4-diethylamino)cyclohexylcarbodiimide, etc., are preferably used as condensing agent, and if necessary an organic base such as 4-pyrrolidinopyridine, pyridine, triethyl-amine and the like is used concurrently.

The condensing agent is used usually in an amount of 1 to 1.2 equivalent to the aliphatic carboxylic acid. In case of using an organic base concurrently, the amount thereof used is usually 0.01 to 0.2 equivalent to said condensing agent.

Such alkylation or acylation reaction is carried out at a temperature or usually −30° to 100° C., preferably −25° to 80° C.

The reaction time is not specified; the moment when the optically active alcohol (III) used as starting material has disappeared may be supposed as the end point of the reaction.

The reaction mixture is subjected to the ordinary separating operations such as extraction, separation of liquid phase, concentration, etc., whereby an optically active benzyl derivative (II) can be obtained in a high yield. If necessary, the product may be purified by column chromatography, recrystallization or other means, but the reaction mixture can be subjected in the form as it is to the treatment of the next step.

The optically active alcohols (III) used as starting material in this reaction can be produced by subjecting the esters represented by the formula (V):

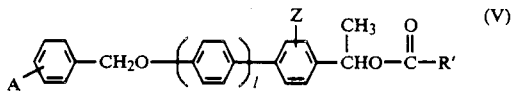

(wherein A, Z and l have the meanings given above, and R' is lower alkyl) to asymmetric hydrolysis by using an esterase having the ability to hydrolyze one of the enantiomers of said esters.

As the microorganism producing the esterase used in the above reaction, there can be employed any of those microorganisms which are capable of producing an esterase having the ability to effectuate asymmetric hydrolysis of said esters (V).

When the term "esterase" is used in this invention, it means esterases of the broad sense including lipase.

Examples of such esterase-producing microorganisms are those belonging to the general Enterobacter, Arthobacter, Brevibacterium, Pseudomonas, Alcaligenes, Micrococcus, Chromobacterium, Microbacterium, Corynebacterium, Bacillus, Lactobacillus, Trichoderma, Candida, Saccharomyces, Rhodotorula, Cryptococcus, Torulopsis, Pichia, Penicillium, Aspergillus, Rhizopus, Mucor, Aureobasidium, Actinomucor, Nocardia, Streptomyces, Hansenula and Achromobacter.

For culture of these microorganisms, usually liquid culture is carried out according to a conventional method. For example, a sterilized liquid medium [a malt extract-yeast extract medium (prepared by dissolving 5 g of peptone, 10 g of glucose, 3 g of malt extract and 3 g of yeast extract in 1 liter of water, with pH adjusted to 6.5) for culture of mold and yeast fungi or a sweetened bouillon medium (prepared by dissolving 10 g of glucose, 5 g of peptone, 5 g of meat extract and 3 g of NaCl in 1 liter of water, with pH adjusted to 7.2) for culture of bacteria] is inoculated with microorganisms and subjected to reciprocal shaking culture usually at 20°–40° C. for 1–3 days. If necessary, solid culture may be employed.

Some of the esterases usable in the reaction of this invention are commercially available. The following can be mentioned as examples of such commercially available esterases: Lipase P (lipase derived from the Pseudomonas, available from Amano Pharmaceutical Co., Ltd.), Lipase AP (lipase derived from the Aspergillus, available from Amano Pharmaceutical Co., Ltd.), Lipase M-AP (lipase derived from the Mucor, available from Amano Pharmaceutical Co., Ltd.), Lipase MY (lipase derived from Candida cylindlasse, available from Meito Sangyo Co., Ltd.), Lipase PL (lipase derived from the Alcaligenes, available from Meito Sangyo), Lipase AL (lipase derived from the Achromobacter, available from Meito Sangyo), Lipase Godo BSL (lipase derived from the Arthrobacter, available from Godo Shusei Co., Ltd.), lipase derived from the Chromobacterium (available from Toyo Brewage Co., Ltd.), Talipase (lipase derived from the Rhizopus delemar, available from Tanabe Pharmaceutical Co., Ltd.), and Lipase Saiken (lipase derived from the Rhizopus, available from Osaka Bacterial Research Institute).

It is also possible to use animal and plant esterases such as steapsin, pancreatin, swine liver esterase, wheat germ esterase, etc.

Enzymes obtained from animals, plants and microorganisms can be used as esterase in the reaction of this invention, and such enzymes can be used in the various forms as desired, such as purified enzyme, crude enzyme, enzyme-containing substance, liquid culture of microorganism, culture, bacterial body, culture filtrate and their treated products. Combinations of enzymes and microorganisms are also usable. Further, immobilized enzymes or immobilized bacterial bodies, in which the enzymes or bacterial bodies have been fixed to a resin, etc., can be used.

The asymmetric hydrolysis reaction is carried out by vigorously stirring a mixture of the starting ester (V) and said enzyme or microorganism usually in a buffer solution.

The buffer solution used in this reaction may be a commonly used buffer solution of an inorganic acid salt such as sodium phosphate, potassium phosphate, etc., or an organic acid salt such as sodium acetate, sodium citrate, etc. The pH of the buffer solution is preferably 8 to 11 in the case of cultures of alkaliphilic bacteria or alkaline esterases and 5 to 8 in the case of cultures of non-alkaliphilic microorganisms or esterases having no alkali resistance. The concentration of the buffer solution is usually in the range of 0.05 to 2 M, preferably 0.05 to 0.5 M.

The reaction temperature is usually 10 to 60° C. and the reaction time is usually 10 to 70 hours, through they are not defined in these ranges.

After such hydrolysis reaction has been completed, the optically active alcohol (III) which is the hydrolyzate and the non-hydrolyzed optical active substance of said starting ester (V), or optical active ester, are separated by extracting the reaction solution with a solvent such as methyl isobutyl ketone, ethyl acetate, ethyl ether, etc., distilling off the solvent from the organic layer and subjecting the concentrated residue to column chromatography, or by other methods.

The optical active ester obtained here may if necessary be further hydrolyzed to be turned into an optical active alcohol which is an enantiomer of the previously obtained optical active alcohol (III).

It is be noted that in case of using a lipase belonging to the genus Pseudomonas or Arthrobacter in said asymmetric hydrolysis reaction, it is possible to obtain an optical active alcohol (III) with a relatively high optical purity.

In this hydrolysis reaction, it is also possible to use an organic solvent inert to the reaction, it is also possible to use an organic solvent inert to the reaction, such as toluene, chloroform, methyl isobutyl ketone, dichloromethane, etc., in addition to the buffer solution. Use of such organic solvent allows advantageous proceeding of the asymmetric hydrolysis.

The esters (V) used as starting material in the above reaction can be easily prepared by reacting the alcohols represented by the formula (VI):

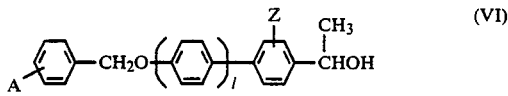

(wherein A, Z and l are as defined above) with lower alkylcarboxylic acids to effect acylation of said alcohols.

The lower alkylcarboxylic acids used in the above acylation reaction are preferably acid anhydrides or acid halides of lower alkylcarboxylic acids, the typical examples thereof being acetic anhydride, acetic acid chloride or bromide, propionic anhydride, propionic acid chloride or bromide, butyryl chloride or bromide, valeryl chloride or bromide, and the like.

The amount of lower alkylcarboxylic acid to be used in the above reaction should be not less than one equivalent to the alcohol (VI). Its upper threshold amount is not subject to any definite limitation, but it is preferably 4 equivalents to said alcohol (VI).

This reaction is carried out in the presence or absence of a solvent by using a catalyst.

Where a solvent is used in this reaction, such solvent is selected from those which are inert to the reaction, for example, aliphatic or aromatic hydrocarbons, ethers and halogenated hydrocarbons, such as tetrahydrofuran, ethyl ether, acetone, methyl ethyl ketone, toluene, benzene, chloroform, chlorobenzene, dichloromethane, dichloroethane, carbon tetrachloride, dimethylformamide and hexane, which may be used either singly or in combination. The amount of such solvent to be used in the reaction is not specifically defined.

As the catalyst, organic or inorganic basic materials such as dimethylaminopyridine, diethylaminopyridine, triethylamine, tri-n-butylamine, pyridine, picoline, imidazole, sodium carbonate and potassium hydrogencarbonate can be used. Organic or inorganic acids such as toluenesulfonic acid, methanesulfonic acid, sulfuric acid, etc., are also usable as catalyst.

The amount of the catalyst to be used in the reaction varies according to the type of lower alkylcarboxylic acid used, combination thereof with the catalyst used and other factors, but in case of using an acid halide of lower alkylcarboxylic acid, the catalyst should be used in an amount of at least one equivalent to said acid halide.

The reaction temperature is usually −30° C. to 100° C., preferably −20° C. to 90° C.

No particular limit is imposed on the reaction time. The moment at which the starting alcohol (VI) has vanished may be supposed to be the end point of the reaction.

After the end of the reaction, the reaction mixture is subjected to the ordinary separating operations such as extraction, separation of liquid phase, concentration, recrystallization, etc., by which the desired ester can be obtained in a high yield. If necessary the product may be purified by column chromatography or other means.

The reaction mixture, however, may be supplied in the form as it is to the next working step.

The alcohols (VI) used as starting material in the above reaction can be produced by reducing the ketones represented by the formula (VII):

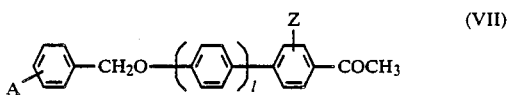

(wherein A, Z and l are as defined above) by using a reducing agent which is capable of reducing ketones into alcohols.

As the reducing agent in the above reaction, sodium borohydride, lithium aluminum hydride, triisopropoxyaluminum or boranes is preferably used in an amount not less than one equivalent, usually 1 to 10 equivalents to the starting ketone (VII).

This reaction is usually carried out in a solvent. As the solvent, there can be used those which are inert to the reaction, for example, ethers such as tetrahydrofuran, dioxane, ethyl ether, etc.; alcohols such as methanol, ethanol, n-propyl alcohol, isopropyl alcohol, etc.; aromatic hydrocarbons such as toluene, benzene, etc.; and halogenated hydrocarbons such as chloroform, dichloromethane, etc. These solvents may be used either singly or in a suitable combination.

The reaction temperature may be selected from the range from −30° C. to 100° C., but the range from −20° C. to 90° C. is preferred.

The alcohols (VI) can be obtained in a high yield from said reaction mixtures by subjecting them to such treatments as separation, concentration, distillation and crystallization. For producing the esters (V), it is not always necessary to isolate the alcohols (VI) and the reaction mixture may be immediately subjected to the next ester forming step.

The ketones (VII) used as starting material in this reaction can be easily produced, for instance, by reacting benzyl halides and acetophenone derivative:

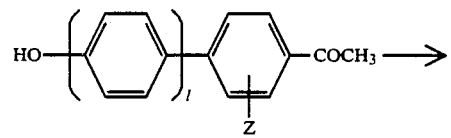

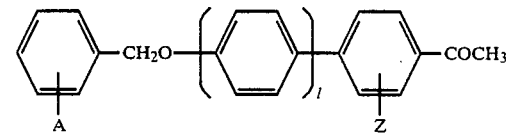

Thus, the novel optically active benzene derivatives represented by the formula (I) can be easily produced according to the process of this invention, and such benzene derivatives are very useful as an intermediate for the preparation of pharmaceuticals, agricultural chemicals, etc., especially as an intermediate for the preparation of liquid crystal material.

DESCRIPTION OF THE PREFERRED EMBODIMENTS

The present invention will be further described below with reference to the examples thereof.

EXAMPLE 1

180.9 g (0.8 mol) of 4-benzyloxyacetophenone (VII-1), 600 ml of tetrahydrofuran and 200 ml of methanol were supplied to a four-necked flask equipped with a stirrer and a thermometer. Then 30.28 g (0.8 mol) of sodium borohydride was added at 15°–25° C. over a period of 2 hours. After kept at the same temperature for 5 hours, the mixture was poured into ice-water and extracted twice with 1,000 ml of ethyl acetate. The organic layer was concentrated under reduced pressure to obtain 177.0 g of 4-benzyloxy-1-phenethyl alcohol (VI-1) in a 97% yield.

136.88 g (0.6 mol) of VI-1 was dissolved in a mixed solution of 600 ml of toluene and 100 ml of pyridine, and then 51.82 g (0.66 mol) of acetyl chloride was added at 15°–20° C. over a period of 2 hours. The mixture was kept at the same temperature for one hour and then at 40°–50° C. for 2 hours.

The reaction mixture was cooled below 10° C. and added with 400 ml of water. After separating the liquid phase, the organic layer was washed with a 2N hydrochloric acid solution, water, 5% sodium carbonate and water successively in that order, then concentrated under reduced pressure and purified by column chromatography to give 159.6 g (98.5% yield) of acetic ester of 4-benzyloxy-1-phenethyl alcohol (V-1).

135.0 g (0.5 mol) of V-1 was mixed with 1,500 ml of a 0.3M phosphate buffer solution (pH 7.5) and 13.5 g of Amano Lipase P and vigorously stirred at 40°–45° C. The reaction mixture was extracted with 1,000 ml of ethyl acetate. The organic layer was concentrated under reduced pressure and the residue was purified by column chromatography using a 5:2 mixed solution of toluene and ethyl acetate as eluting solvent to give 46.7 g (41% yield) of (+)-4-benzyloxy-1-phenethyl alcohol (III-1) ($[\alpha]_D^{20} = +35.9°$ (c=1, CHCl$_3$), m.p.=66°–68° C.) and 74.8 g of unreacted ester ($[\alpha]_D^{20} = -93°$ (c=1, CHCl$_3$), m.p.=52°–55° C.).

A solution of 3.42 g (0.015 mol) of III-1 and 40 ml of dimethylformamide was cooled to 10° C., then added with 0.47 g (0.0196 mol) of sodium hydride and kept at 30°–35° C. for one hour. The mixture was then added with 4.82 g (0.0225 mol) of n-propyl tosylate at 20°–25° C. and reacted at 30°–40° C. for 5 hours. The reaction mixture was poured into ice-water and extracted with 100 ml of ethyl acetate. The organic layer was washed with water and concentrated under reduced pressure, and the residue was purified by column chromatography to obtain 3.31 g (94% yield) of (+)-4-benzyloxy-1-(1'-propoxyethyl)benzene (II-1) ($[\alpha]_D^{20} = +70.8°$ (c=1, CHCl$_3$), m.p.=51°–53° C.).

3.51 g (0.013 mol) of II-1 was mixed with 10 ml of methanol and 0.2 g of 5% Pd-carbon, and the mixture was subjected to catalytic hydrogenation in a hydrogen atmosphere under normal pressure. When the hydrogen absorption reached 300 ml, the reaction was stopped and the catalyst was filtered away. The filtrate was concentrated and the residue was purified by column chromatography using a 5:2 mixture of toluene and ethyl acetate as eluent to give 2.18 g (93% yield) of (+)-4-(1'-propoxyethyl)phenol ($[\alpha]_D^{20} = +85.6°$ (c=1, CHCl$_3$), m.p.=61°–63° C.).

EXAMPLE 2

A solution of 3.42 g (0.015 mol) of III-1 obtained in Example 1 and 30 ml of N-methylpyrrolidone was cooled to 5° C. and added with 0.72 g (0.03 mol) of sodium hydride. The mixture was kept at 30°–35° C. for one hour, then added with 5.32 g (0.0375 mol) of methyl iodide at 15°–20° C. and reacted at 20°–30° C. for 2 hours and further at 40°–50° C. for additional 2 hours. The reaction mixture was poured into ice-water and extracted with 50 ml of ethyl acetate. The extract was purified according to the method of Example 1 to obtain 3.49 g (96% yield) of (+)-4-benzyloxy-1-(1'-methoxyethyl)benzene (II-2) ($[\alpha]_D^{20} = +77.6°$ (c=1, CHCl$_3$), $n_D^{20}=1.5432$).

2.42 g (0.01 mol) of II-2 was mixed with 15 ml of tetrahydrofuran and 0.2 g of 5% Pd-carbon and subjected to catalytic hydrogenation in a hydrogen atmosphere under normal pressure. When the hydrogen absorption reached 240 ml, the reaction was stopped and the catalyst was filtered away. The filtrate was concentrated and the residue was purified by column chromatography to obtain 1.48 g (98% yield) of (+)-4-(1'-methoxyethyl)phenol. ($[\alpha]_D^{20} = +106.1°$ (c=1, CHCl$_3$), m.p.=114°–115° C.).

EXAMPLE 3

A solution of 3.42 g (0.015 mol) of III-1 obtained in Example 1 and 40 ml of dimethylformamide was cooled to 10° C., then added with 0.47 g (0.0196 mol) of sodium hydride and kept at 30°–35° C. for one hour. Then 5.76 g (0.0225 mol) of n-hexyl tosylate was added and the mixture was reacted at 40°–45° C. for 5 hours. The reaction mixture was further treated according to Example 1 to obtain 4.42 g (94.5% yield) of (+)-4-benzyloxy-1-(1'-n-hexyloxyethyl)benzene (II-3). ($[\alpha]_D^{20} = +58.9°$ (c=1, CHCl$_3$), $n_D^{20}=1.5230$).

3.12 g (0.01 mol) of II-3 was mixed with 15 ml of methanol and 0.3 g of 5% Pd-carbon, and the mixture was subjected to catalytic hydrogenation in a hydrogen atmosphere under normal pressure. When the hydrogen absorption reached 240 ml, the reaction was stopped and the catalyst was filtered away. The filtrate was concentrated and the residue was purified by column chromatography to give 2.13 g (96% yield) of (+)-4-(1'-n-hexyloxyethyl)phenol. ($[\alpha]_D^{20} = +72.5°$ (c=1, CHCl$_3$), $n_D^{20}=1.5060$).

EXAMPLE 4–8

The procedure of Example 3 was followed except that n-hexyl tosylate was replaced by the alkylating agents shown in Table 1. The results are shown in Table 1.

EXAMPLE 9

13.5 g (50 mmol) of unreacted ester obtained along with III-1 in Example 1 was added to a solution of 50 ml of methanol, 30 ml of 20% sodium hydroxide and 30 ml of tetrahydrofuran and stirred at 30°–40° C. for 2 hours. The reaction solution was added with 200 ml of water, adjusted to pH 6 with 4N hydrochloric acid and extracted with 500 ml of ether. The organic layer was washed with water and concentrated under reduced pressure to give 11.2 g (98% yield) of (−)-4-benzyloxy-1-phenethyl alcohol as a white solid.

3.42 g (15 mmol) of this product was further treated according to Example 8 to obtain 4.02 g (91% yield) of (−)-4-benzyloxy-1-(1'-(s)-2-methylbutyloxyethyl)benzene (II-9). Melting point=46.5°–47.5° C. $[\alpha]_D^{20} = -48.2°$ (c=1, CHCl$_3$). II-9 was debenzylated in the same way as in Example 8 to obtain the results shown in Table 1.

1-(1'-((s)-2-chloropropoxy)ethyl)benzens (II-10). $[\alpha]_D^{20} = +73.8°$ (c=1, CHCl$_3$), m.p.=42°–44° C.

1.0 g of II-10 was mixed with 20 ml of methanol and 0.1 g of 5% Pd-carbon, and the mixture was subjected to catalytic hydrogenation in a hydrogen atmosphere under normal pressure. When the hydrogen absorption reached the equivalence point, the reaction was stopped

TABLE 1

| Example No. | Alkylating agent Compound name | Amount used | Compound of formula (II) Yield | Properties | Produced compound of formula (I) R | l | Z | n | Yield | Properties |
|---|---|---|---|---|---|---|---|---|---|---|
| 4 | n-octyl tosylate | 6.39 g (0.0225 mol) | 4.85 g (95%) | $n_D^{20}$ 1.5157 $[\alpha]_D^{20}$ +55.1° | -n-C$_8$H$_{17}$ | 0 | H | 0 | 2.41 g (96.5%) | $n_D^{20}$ 1.5010 $[\alpha]_D^{20}$ +69.2° |
| 5 | n-dodecyl tosylate | 7.65 g (0.0225 mol) | 5.57 g (93.5%) | $n_D^{20}$ 1.4982 $[\alpha]_D^{20}$ +40° | -n-C$_{12}$H$_{25}$ | 0 | H | 0 | 2.97 g (97.0%) | m.p. 53–54° C. $[\alpha]_D^{20}$ +50° |
| 6 | ω-ethoxypropyl tosylate | 5.8 g (0.08 mol) | 4.24 g (90%) | $n_D^{20}$ 1.5336 $[\alpha]_D^{20}$ +72.5° | —C$_3$H$_6$OC$_2$H$_5$ | 0 | H | 0 | 2.16 g (96.6%) | $n_D^{20}$ 1.5096 $[\alpha]_D^{20}$ +86.9° |
| 7 | Methoxyethyl tosylate | 6.9 g (0.03 mol) | 3.86 g (90%) | $n_D^{20}$: 1.5354 $[\alpha]_D^{20}$: +43.6° (c = 1, CHCl$_3$) | —C$_2$H$_4$OCH$_3$ | 0 | H | 0 | 1.79 g (91.5%) | $n_D^{20}$ 1.5111 $[\alpha]_D^{20}$: +71.1° (c = 1, CHCl$_3$) |
| 8 | (s)-2-methylbutyl tosylate | 5.5 g (0.0225 mol) | 4.11 g (92%) | M.p. = 48–50° C. $[\alpha]_D^{20}$: +74.4° (c = 1, CHCl$_3$) | CH$_3$ \| —CH$_2$CHC$_2$H$_5$ | 0 | H | 0 | 1.95 g (94%) | $n_D^{20}$ 1.5060 $[\alpha]_D^{20}$: +86.5° (c = 1, CHCl$_3$) |
| 9 | (s)-2-methylbutyl tosylate | 5..5 g (0.0225 mol) | 4.01 g (90%) | M.p. = 46.5 –47.5° C. $[\alpha]_D^{20}$: −48.2° (c = 1, CHCl$_3$) | CH$_3$ \| —CH$_2$CHC$_2$H$_5$ | 0 | H | 0 | 2.0 g (96%) | $n_D^{20}$ 1.5101 $[\alpha]_D^{20}$: −71.5° (c = 1, CHCl$_3$) |

EXAMPLE 10

24.0 g (0.1 mol) of 4-(4-methylbenzyloxy)acetophenone (VII-10), 100 ml of chloroform and 30 ml of methanol were supplied into the same flask as used in Example 1, after which 4.5 g (0.12 mol) of sodium borohydride was added at 15°–20° C. over a period of 2 hours. The mixture was kept at the same temperature for 5 hours, then poured into ice-water and extracted with chloroform. The organic layer was concentrated under reduced pressure to obtain 23.1 g (95.5% yield) of 4-(4-methylbenzyloxy)-1-phenethyl alcohol (VI-10).

18.16 g (0.075 mol) of VI-10 was mixed with 100 ml of toluene and 15 ml of pyridine, and to this mixed solution was added 6.48 g (82.5 mmol) of acetyl chloride at 10°–20° C. over a period of 2 hours. The mixture was kept at the same temperature for one hour and then at 40°–50° C. for 2 hours. It was then treated and purified according to Example 1 to obtain 20.78 g (97.5% yield) of acetic ester of 4-(4-methylbenzyloxy)-1-phenethyl alcohol (V-10).

19.2 g (70 mmol) of V-10 was mixed with 200 ml of 0.3M phosphate buffer (pH 7.0) and 2.88 g of Lipase P, and the mixture was stirred vigorously at 35°–40° C. for 20 hours. The reaction mixture was treated and purified according to Example 1 to obtain 6.6 g (39% yield) of (+)-4-(4-methylbenzyloxy)-1-phenethyl alcohol (III-10). $[\alpha]_D^{20}=+34.2°$ (c=1, CHCl$_3$), m.p.=52°–53° C.).

A solution of 1.2 g (0.005 mol) of III-10 and 20 ml of N-methylpyrrolidone was cooled to 10° C., added with 0.17 g (0.007 mol) of sodium hydride and kept at 30°–35° C. for one hour. Then 1.7 g (0.007 mol) of (s)-2-chloropropyl tosylate was added and the mixture was reacted at 40°–45° C. for 4 hours. The reaction mixture was poured into ice-water and extracted with 200 ml of toluene. The organic layer was washed with water and concentrated under reduced pressure, and the residue was purified by silica gel column chromatography to obtain 1.38 g (92% yield of (+)-4-(4-methylbenzyloxy)- and the catalyst was filtered away. The filtrate was concentrated and the residue was purified by column chromatography using a toluene-ethyl acetate mixed solution as eluent to obtain 0.56 g (84% yield) of (+)-4-(1-((s)-2-chloropropoxy)ethyl)phenol. $[\alpha]_D^{20}=+93°$ (c=1, CHCl$_3$), m.p.=50°–51° C.

EXAMPLE 11

The procedure of Example 10 was followed except that 25.6 g (0.1 mol) of 4-(4-methoxybenzyloxy)acetophenone (VII-11) was used in place of 4-(4-methylbenzyloxy)acetophenone to obtain 4-(4-methoxybenzyloxy)-1phenethyl alcohol (VI-11) in a 97% yield.

By using VI-11 in place of VI-10, the procedure of Example 10 was repeated on the same molar scale to obtain acetic ester of 4-(4-methoxybenzyloxy)-1-phenethyl alcohol (VI-11) (96% yield).

By using V-11 in place of V-10, the procedure of Example 10 was followed on the same molar scale to obtain (+)-4-(4-methoxybenzyloxy)-1-phenethyl alcohol (III-11) (35% yield).

By using 1.29 g (0.005 mol) of III-11 in place of III-10 and by using 2.8 g (0.008 mol) of n-octadecyl bromide in place of (s)-2-chloropropyl tosylate, the procedure of Example 10 was followed to obtain 2.3 g of (+)-4-(4-methoxybenzyloxy)-1-(1-octadecyloxyethyl)benzene (II-11) (90% yield).

By using II-11 in place of II-10, the same treatments (catalytic hydrogenation, etc.) as in Example 10 were carried out to obtain 0.73 g of (+)-4-(1-octadecyloxyethyl)phenol (89% yield). $[\alpha]_D^{20}=+31.1°$ (c=1, chloroform), $n_D^{20}=1.4990$.

EXAMPLE 12

120.9 g (0.4 mol) of 4-benzyloxy-4'-acetylbiphenyl, 400 ml of tetrahydrofuran and 100 ml of methanol were supplied into a four-necked flask provided with a stirrer and a thermometer. Then 15.14 g (0.4 mol) of sodium borohydride was added at 15°–25° C. over a period of 2 hours. The mixture was kept at the same temperature for 5 hours, then poured into ice-water and extracted twice with 500 ml of chloroform. The organic layer was concentrated under reduced pressure to obtain 117.4 g (96.5% yield) or 4-benzyloxy-4'-(1-hydroxyethyl)-biphenyl (VI-12).

91.25 g (0.3 mol) of VI-12 was dissolved in a mixed solution of 400 ml of toluene and 100 ml of pyridine, and then 25.91 g (0.33 mol) of acetyl chloride was added at 15°-20° C. over a period of 2 hours. After the reaction was completed, the reaction mixture was cooled below 10° C. and then added with 300 ml of water. The mixture was kept at the same temperature for one hour and then at 40°-50° C. for 2 hours. 400 ml of water was added in the reaction mixture. After separating the liquid phase, the organic layer was washed with a 2N hydrochloric acid solution, water, 5% sodium carbonate and water in this order successively, then concentrated under reduced pressure and purified by column chromatography to give 101.57 g (97.8% yield) of 4-benzyloxy-4'-(1-acetoxyethyl)-biphenyl (V-12).

86.55 g (0.25 mol) of V-12 was mixed with 2,000 ml of 0.3M phosphate buffer (pH 7.5) and 50 g of Amano Lipase P and stirred vigorously at 40°–45° C. for 120 hours. The reaction mixture was extracted with 1,000 ml of chloroform. The organic layer was concentrated under reduced pressure and the residue was purified by column chromatography using a 5:2 mixture of toluene and ethyl acetate as eluent to obtain 28.9 g (38% yield) of (+)-4-benzyloxy-4'-(1-hydroxyethyl)-biphenyl biphenyl (III-12) ($[\alpha]_D^{20}=+34.8°$ (c=1, CHCl$_3$), m.p.=158°-159° C.) and 50.17 g of unreacted ester.

A solution of 4.56 g (0.015 mol) of III-12 in 40 ml of dimethylformamide was cooled to 10° C., added with 0.47 g (0.0196 mol) of sodium hydride and kept at 30°-35° C. for one hour. Then 4.82 g (0.0225 mol) of n-propyl tosylate was added at 20°-25° C. and the mixture was reacted at 30°-40° C. for 5 hours. The reaction mixture was poured into ice-water and extracted with 200 ml of chloroform. The organic layer was washed with water and concentrated under reduced pressure. The residue was purified by column chromatography to obtain 4.91 g (94.5% yield) of (+)-4-benzyloxy-4'-(1-propoxyethyl)-biphenyl (II-12) ($[\alpha]_D^{20}=+73.7°$ (c=1, CHCl$_3$), m.p.=106°-108° C.).

3.46 g of II-12 was mixed with 20 ml of methanol and 0.3 g of 5% Pd-carbon, and the mixture was subjected to catalytic hydrogenation in a hydrogen atmosphere under normal pressure. When the hydrogen absorption reached 240 ml, the reaction was stopped and the catalyst was filtered away. The filtrate was concentrated and the residue was purified by column chromatography using a 5:2 mixture of toluene and ethyl acetate as eluent to obtain 2.43 g (94.8% yield) of (+)-4-hydroxy-4'-(1-propoxyethyl)-biphenyl ($[\alpha]_D^{20}=+94.5°$ (c=1, CHCl$_3$), m.p.=123°-125° C.).

EXAMPLE 13

A solution of 4.56 g (0.015 mol) of III-12 obtained in Example 12 in 30 ml of N-methylpyrrolidone was cooled to 5° C., then added with 0.72 g (0.03 mol) of sodium hydride and kept at 30°-35° C. for one hour.

Then the mixed solution was further added with 5.32 g (0.0375 mol) of methyl iodide at 15°-20° C. and reacted at 40°-50° C. for 2 hours. The resulting reaction mixture was poured into ice-water and extracted with 50 ml of ethyl acetate. The extract was further treated and purified according to Example 12 to obtain 4.61 g (96.5% yield) of (+)-4-benzyloxy-4'-(1-methoxyethyl)-biphenyl ethyl)-biphenyl (II-13) ($[\alpha]_D^{20}=+77.3°$ (c=1, CHCl$_3$), m.p.=97°-98° C.).

3.18 g (0.01 mol) of II-13 was mixed with 15 ml of tetrahydrofuran and 0.3 g of 5% Pd-carbon, and the mixture was subjected to catalytic hydrogenation in a hydrogen atmosphere under normal pressure. When the hydrogen absorption reached 240 ml, the reaction was stopped and the catalyst was filtered away. The filtrate was concentrated and the residue was purified by column chromatography to obtain 2.2 g (96.7% yield) of (+)-4-hydroxy-4'-(1-methoxyethyl)biphenyl ($[\alpha]_D^{20}=104.1°$ (c=1, CHCl$_3$), m.p.=174°-175° C.).

EXAMPLE 14

A solution consisting of 4.56 g (0.015 mol) of III-12 obtained in Example 12 and 40 ml of dimethylformamide was cooled to 10° C., added with 0.47 g (0.0196 mol) of sodium hydride and kept at 30°-35° C. for one hour. Then 5.76 g (0.0225 mol) of n-hexyl tosylate was added and the mixture was reacted at 40°-45° C. for 5 hours. The reaction mixture was further treated according to Example 12 to obtain 5.5 g (94.4% yield) of (+)-4-benzyloxy-4'-(1-n-hexyloxyethyl)biphenyl (II-14) $[\alpha]_D^{20}=+37.8°$ (c=1, CHCl$_3$), m.p.=61°-63° C.).

3.88 g (0.01 mol) of II-14 was mixed with 10 ml of tetrahydrofuran, 15 ml of methanol and 0.3 g of 5% Pd-carbon, and the mixture was subjected to catalytic hydrogenation in a hydrogen atmosphere under normal pressure. When the hydrogen absorption reached 240 ml, the reaction was stopped and the catalyst was filtered away. The filtrate was concentrated and the residue was purified by column chromatography to obtain 2.83 g (94.8% yield) of (+)-4-hydroxy-4'-(1-n-hexyloxyethy)bipheny ($[\alpha]_D^{20}=+32.8°$ (c=1, CHCl$_3$), $n_D^{20}=1.5506$).

EXAMPLES 15 and 16

The procedure of Example 14 was followed except that III-12 was used as starting material and that n-hexyl tosylate was replaced by the alkylating agents shown in Table 2. The results are shown in Table 2.

TABLE 2

| Example No. | Alkylating agent | | Compound of formula (II) | | Produced compound of formula (I) | | | | | |
|---|---|---|---|---|---|---|---|---|---|---|
| | Compound name | Amount used | Yield | Properties | R | l | Z | n | Yield | Properties |
| 15 | n-octyl tosylate | 7.65 g (0.0225 mol) | 5.93 g (95%) | m.p. 54-55° C. $[\alpha]_D^{20}+33.2°$ (c = 1, CHCl$_3$) | -n-C$_8$H$_{17}$ | 1 | H | 0 | 3.11 g (95.4 g) | $n_D^{20}$ 1.5432 $[\alpha]_D^{20}+36.9°$ (c = 1, CHCl$_3$) |
| 16 | Ethoxypropyl tosylate | 5.8 g (0.03 mol) | 5.32 g (91%) | $n_D^{20}=1.5444$ $[\alpha]_D^{20}=+41.6°$ (c = 1, CHCl$_3$) | —C$_3$H$_6$OC$_2$H$_5$ | 1 | H | 0 | 2.67 g (89%) | $n_D^{20}$ 1.5496 $[\alpha]_D^{20}+40.3°$ (c = 1, CHCl$_3$) |

EXAMPLE 17

134.6 g (0.4 mol) of 4-acetyl-4'-(4-chlorobenzyl)oxybiphenyl, 100 ml of methanol and 450 ml of tetrahydrofuran were supplied into a four-necked flask equipped with a stirrer and a thermometer. Then 15.1 g (0.4 mol) of sodium borohydride was added at 15°–25° C. over a period of 2 hours and the mixture was kept at the same temperature for 5 hours.

The reaction mixture was poured into ice-water and extracted twice with 500 ml of chloroform. The organic layer was washed with water and concentrated under reduced pressure to give 135.1 g (approx. 100% yield) of 4-(1-hydroxyethyl)-4'-(1-chlorobenzyl)oxybiphenyl (VI-17) having a melting point of 170.5°14 172° C.

101.5 g (0.3 mol) of VI-17 was dissolved in a mixed solution of 400 ml of toluene and 100 ml of pyridine, to which 25.9 g (0.33 mol) of acetyl chloride was added at 15°–20° C. over a period of 2 hours. The mixture was kept at the same temperature for one hour and then at 40°–50° C. for 2 hours. The reaction mixture was cooled below 10° C. and added with 300 ml of water. Liquid phase was separated and the organic layer was washed with a 2N hydrochloric acid solution, water, 5% sodium carbonate and water in that order successively and concentrated under reduced pressure to obtain 101.6 g (97.8% yield) of 4-(1-acetoxyethyl)-4'-(4-chlorobenzyl)oxybiphenyl (V-17).

15.1 g of V-17 was mixed with 0.5 liter of 0.3M phosphate buffer (pH 7.5) and 5 g of Lipase (32) P and stirred vigorously at 40°–45° C. for 5 days. The resulting reaction mixture was extracted with 0.5 liter of chloroform. The organic layer was concentrated under reduced pressure and the residue was purified by column chromatography using toluene-ethyl acetate as eluting solvent to obtain 5.8 g (42.5% yield) of (+)-4-(1-hydroxyethyl)-4'-(4-chlorobenzyl)oxybiphenyl (III-17) ([α]$_D^{20}$=+30.2° (c=1, chloroform), m.p.=165°–167° C.).

A solution of 1.35 g (4 mmol) of III-17 in 20 ml of dimethylformamide was cooled to 10°–15° C., added with 0.2 g (5 mmol) of sodium hydride and kept at 30°–40° C. for one hour. The mixture was further added with 2.0 g (5 mmol) of n-hexadecyl tosylate and reacted for 3 hours. The reaction mixture was poured into ice-water and extracted with 300 ml of toluene. The organic layer was washed with water and concentrated under reduced pressure. The residue was purified by silica gel column chromatography using toluene-hexane as eluting solvent to give 2.07 g (92% yield) of (+)-4-(1-hexadecyloxyethyl)-4'-(4-chlorobenzyl)oxybiphenyl (II-17) ([α]$_D^{20}$=+19.8° (c=1, chloroform), m.g.=22°–30° C.).

1.0 g (0.0018 mol) of II-17 was mixed with 10 ml of tetrahydrofuran, 15 ml of methanol and 0.1 g of 5% Pd-carbon, and the mixture was subjected to catalytic hydrogenation in a hydrogen atmosphere under normal pressure. When the hydrogen absorption reached the equivalence point, the reaction was stopped and the catalyst was filtered away. The filtrate was concentrated and the residue was purified by column chromatography to obtain 0.68 g (87% yield) of (+)-4-hydroxy-4'-(1-n-hexadecyloxyethyl)biphenyl. [α]$_D^{20}$=+25.1° (c=1, CHCl$_3$), n$_D^{20}$=1.5398.

EXAMPLES 18 AND 19

The procedure of Example 17 was followed except that III-17 was used as starting material and that n-hexadecyl tosylate was replaced by the alkylating agents shown in Table 3. The results are shown in Table 3.

TABLE 3

| Example No. | Alkylating agent Compound name | Amount used | Compound of formula (II) Yield | Properties | Produced compound of formula (I) R | l | Z | n | Yield | Properties |
|---|---|---|---|---|---|---|---|---|---|---|
| 18 | 2(s)-chloropropyl tosylate | 1.24 g (5 mmol) | 1.53 (92%) | m.p. 116–118° C. [α]$_D^{20}$ +78.7° (c = 1, CHCl$_3$) | Cl \| —CH$_2$CHCH$_3$ | 1 | H | 0 | 0.43 g (82%) | m.p. 120–125° C. [α]$_D^{20}$ +95.5° (c = 1, CHCl$_3$) |
| 19 | 2(s)-methylbutyl tosylate | 1.21 g (5 mmol) | 1.52 g (93%) | m.p. 51–53° C. [α]$_D^{20}$ +56.3° (c = 1, CHCl$_3$) | CH$_3$ \| —CH$_2$CH—CH$_2$CH$_3$ | 1 | H | 0 | 0.46 g (90%) | n$_D^{20}$ 1.5490 [α]$_D^{20}$ +54.8° (c = 1, CHCl$_3$) |

EXAMPLE 20

3.45 g (0.01 mol) of unreacted ester (−)-4-benzyloxy-4'-(1-acetoxyethyl)biphenyl obtained in Example 12 was added into a mixture of 50 ml of methanol and 25 ml of a 20% sodium hydroxide solution and stirred at 30°–40° C. for 2 hours. The reaction mixture was added with 200 ml of water, adjusted to pH 4 with 4N hydrochloric acid and extracted with 500 ml of ether. The organic layer was washed with water and concentrated under reduced pressure to give 3.0 g (99% yield) of (−)-4-benzyloxy-4'-(1-hydroxyethyl)biphenyl as a white solid. By using 1.22 g (4 mmol) of this product as starting material, the alkylation, debenzylation and after-treatments of Example 19 were carried out to obtain 0.47 g (91% yield) of (−)-4-hydroxy-4'-(1-(2s-methylbutyloxy)ethyl)biphenyl. n$_D^{20}$=1.5479, [α]$_D^{20}$=−60.0° (c=1, CHCl$_3$).

EXAMPLE 21

1.14 g (5 mmol) of (+)-4-benzyloxy-1-phenethyl alcohol (III-1) obtained in Example 1 was dissolved in 15 ml of dry pyridine, followed by dropwise addition of 0.51 g (5.5 mmol) of propionic acid chloride. The mixture was stirred at room temperature for one hour, then poured into 100 ml of 2N hydrochloric acid and extracted with 50 ml of toluene. The toluene layer was washed with water, then with a 7% sodium bicarbonate solution and further with water, and then dried over anhydrous magnesium sulfate. The solvent was distilled off from the toluene solution under reduced pressure and the residue was purified by silica gel column chromatography to give 1.4 g (99% yield) of propionic ester of (+)-4-benzyloxy-1-phenethyl alcohol (II-21).

This ester was further purified by recrystallizing it from ethanol. M.p.=52° C., [α]$_D^°$=+93.0° (c=1, CHCl$_3$).

1.14 g (4 mmol) of II-21 obtained here was mixed with 10 ml of methanol and 0.2 g of 5% Pd-carbon, and the mixture was subjected to catalytic hydrogenation in a hydrogen atmosphere under normal pressure. When the hydrogen absorption reached 100 ml, the reaction was stopped and the catalyst was filtered away. The filtrate was concentrated and the residue was purified by column chromatography using a 5:2 mixture of toluene and ethyl acetate as eluent to obtain 0.73 g (93.5% yield) of (+)-4-(1'-propionyloxyethyl)phenol. M.p.=71°-72° C., $[\alpha]_D^{20} = +92°$ (c=1, CHCl$_3$).

EXAMPLE 22

1.14 g (5 mmol) of III-1 obtained in Example 1, 20 ml of toluene, 5 ml of pyridine and 1.18 g (5.5 mmol) of hexanoic anhydride were mixed and reacted at 30°–40° C. for 5 hours. The reaction mixture was poured into ice-water and extracted with 20 ml of toluene. The toluene layer was washed with a 2N hydrochloric acid solution, a 2% sodium bicarbonate solution and water in that order successively, followed by further treatment and purification according to Example 21 to obtain 1.58 g (97% yield) of hexanoic ester of (+)-4-benzyloxy-1-phenethyl alcohol (II-22). $[\alpha]_D^{20} = +73°$ (c=1, CHCl$_3$), $n_D^{25} = 1.5289$.

1.30 g (4 mmol) of II-22 was mixed with 10 ml of methanol and 0.2 g of 5% Pd-carbon, and the mixture was subjected to catalytic hydrogenation in a hydrogen atmosphere under normal pressure. When the hydrogen absorption reached 95 ml, the reaction was stopped and the catalyst was filtered away. The filtrate was concentrated and the residue was purified by column chromatography to obtain 0.85 g (90% yield) of (+)-4-(hexanoyloxyethyl)phenol. $[\alpha]_D^{20} = +79°$ (c=1, CHCl$_3$), $n_D^{25} = 1.5101$.

EXAMPLE 23

12.09 g (0.04 mol) of 4'-acetyl-4-benzyloxybiphenyl (VII-23), 40 ml of tetrahydrofuran and 10 ml of methanol were supplied into a four-necked flask provided with a stirrer and a thermometer. Then 1.51 g (0.4 mol) of sodium boron hydride was added at 15°-25° C. over a period of 2 hours. The mixture was kept at the same temperature for 5 hours, then poured into ice-water and extracted with 50 ml of chloroform. The organic layer was concentrated under reduced pressure to give 11.0 g (95% yield) of 4-benzyloxy-4'-(1-hydroxyethyl)biphenyl (VI-23).

9.0 g (0.03 mol) of 4-benzyloxy-4'-(1hydroxyethyl)biphenyl was dissolved in a mixed solution of 40 ml of toluene and 10 ml of pyridine, followed by addition of 2.59 g (0.033 mol) of acetyl chloride at 15°-20° C. over a period of 2 hours. The mixture was kept at the same temperature for one hour and then at 40°-50° C. for 2 hours.

The reaction mixture was cooled below 10° C. and added with 30 ml of water. After separating the liquid phase, the organic layer was washed with a 1N hydrochloric acid solution, water, 5% sodium carbonate and water in that order successively, then concentrated under reduced pressure and purified by column chromatography to obtain 10.1 g (97% yield) of acetic ester of 4-benzyloxy-4'-(1-hydroxyethyl)biphenyl (V-23).

8.65 g (0.025 mol) of acetic ester of 4-benzyloxy-4'-(1-hydroxyethyl)biphenyl was mixed with 200 ml of 0.3M phosphate buffer (pH 7.5) and 5 g of Amano Lipase P and stirred vigorously at 40°–45° C. for 120 hours. The resulting reaction mixture was extracted with 100 ml of chloroform. The organic layer was concentrated under reduced pressure and the residue was purified by column chromatography using a 5:2 mixture of toluene and ethyl acetate as eluent to obtain 2.89 g of (+)-4-benzyloxy-4'-(1-hydroxyethyl)biphenyl (III-23) ($[\alpha]_D^{20} = +34.8°$ (c=1, CHCl$_3$), m.p.=158°-159° C.).

1.22 g (4 mmol) of III-23 was dissolved in a mixed solution of 10 ml of dichloromethane and 10 ml of pyridine, followed by addition of 0.71 g (4.4 mmol) of octanoic acid chloride at 20° C. The mixture was stirred at the same temperature for 3 hours and then at 40°-50° C. for 2 hours, poured into ice-water and extracted with dichloromethane. The organic layer was washed with a 1N hydrochloric acid solution, a 2% sodium bicarbonate solution and water in that order successively, then concentrated under reduced pressure and purified by silica gel column chromatography to obtain 1.64 g (95.5% yield) of octanoic ester of (+)-4-benzyloxy-4'-(1-hydroxyethyl)biphenyl (II-23). $[\alpha]_D^{25} = +43°$ (c=1, CHCl$_3$), m.p.=92°-93° C.

1.29 g (3 mmol) of II-23 was mixed with 20 ml of tetrahydrofuran, 5 ml of methanol and 0.25 g of 5% Pd-carbon, and the mixture was subjected to catalytic hydrogenation in a hydrogen atmosphere under normal pressure. When the hydrogen absorption reached 70 ml, the reaction was stopped and the catalyst was filtered away. The resulting product was further treated and purified according to Example 21 to obtain 0.9 g (88% yield) of (+)-4-(1'-octanoyloxyethyl)-4'-hydroxybiphenyl. $[\alpha]_D^{25} = +29°$ (c=1, CHCl$_3$), $n_D^{25} = 1.5536$.

EXAMPLE 24

1.22 g (4 mmol) of III-23 obtained in Example 23, 0.72 g (4.8 mmol) of (2s, 3s)-2-chloro-3-methylpentanoic acid and 20 ml of dichloromethane were mixed, followed by addition of 0.91 g (4.4 mmol) of dicyclohexylcarbodiimide and 0.03 g of 4-pyrrolidinopyridine, and the mixture was reacted at room temperature for 10 hours. The precipitated dicyclohexylurea was filtered away. The filtrate was concentrated under reduced pressure and the residue was purified by silica gel column chromatography (using toluene as eluent) to obtain 1.68 g (95.5% yield) of (2s, 3s)-2-chloro-3-methylpentanoic ester of (+)-4-benzyloxy-4'-(1-hydroxyethyl)-biphenyl (II-23). $[\alpha]_D^{25} = +68.3°$ (c=1, CHCl$_3$), m.p.=125°-126° C.

1.31 g (3 mmol) of II-23 was mixed with 10 ml of tetrahydrofuran, 3 ml of toluene and 0.1 g of 2% Pd-carbon, and the mixture was subjected to catalytic hydrogenation in a hydrogen atmosphere. The reaction mixture was filtered to remove the catalyst and further treated and purified according to Example 21 to obtain 0.32 g (31% yield) of (+)-4-hydroxy-4'-(1-2's,3's-2-chloro-3-methylpentanoyl)ethyl)biphenyl.
$[\alpha]_D^{25} = +60°$ (c=1, CHCl$_3$), m.p.=99°-100° C.

EXAMPLE 25

1.21 g (5 mmol) of III-10 obtained in Example 10, 1.65 g (6 mmol) of palmitic acid chloride, 10 ml of pyridine and 10 ml of toluene were mixed and reacted at 25°-30° C. for 10 hours. The reaction mixture was further treated and purified according to Example 21 to obtain 2.16 g (90% yield) of palmitic ester of (+)-p-(4-methylbenzyloxy)-1-phenethyl alcohol (II-23). $[\alpha]_D^{25} = 58°$ (c=1, CHCl$_3$), $n_D^{25} = 1.5186$.

By using 1.86 g (4 mmol) of II-23, the same reaction, treatments and purification as conducted in Example 21 were repeated to obtain 1.41 g (94% yield) of (+)-4-(1'-palmitoyloxyethyl)phenol. $[\alpha]_D^{20} = 58°$ (c=1, CHCl$_3$), waxy solid.

EXAMPLE 26

The procedure of Example 25 was followed except that III-11 obtained in Example 11 was used as starting material and that decanoic acid chloride was used in place of palmitic acid chloride to obtain decanoic was used in place of palmitic acid chloride to obtain decanoic acid ester of (+)-4-(4-methoxybenzyloxy)-phenethyl alcohol (II-26) in a 96% yield.

By using II-26, the same reaction, treatments and purification as performed in Example 21 were carried out to obtain (+)-4-(1'-decanoyloxyethyl)phenol (90% yield). $[\alpha]_D^{25} = +52°$, $n_D^{25} = 1.4912$.

EXAMPLE 27

The procedure of Example 23 was followed except that III-17 obtained in Example 17 was used as starting material and that octanoic acid chloride was replaced by the same molar amount of propionic acid chloride to obtain propionic ester of (+)-4-(4-chlorobenzyloxy-4'-(1-hydroxyethyl)biphenyl (II-27). $[\alpha]_D^{25} = +44°$ (c=1, CHCl$_3$).

By using 3 mmol of II-27, the same catalytic hydrogenation and treatments as conducted in Example 23 were practiced to obtain (+)-4-(1-propionyloxyethyl)4'-hydroxybiphenyl. $[\alpha]_D^{25} = +60°$ (c=1, CHCl$_3$), m.p.=136°-138° C.

EXAMPLES 28-30

The same acylation and after-treatments as conducted in Example 21 were repeated except that the acylating agents (5.5 mmol) shown in Table 4 were used in place of propionic acid chloride.

4 mmol of each of the thus obtained compounds of formula (II) was mixed with 15 ml of tetrahydrofuran, 3 ml of toluene and 0.1 g of 2% Pd-carbon and subjected to catalytic hydrogenation under a hydrogen atmosphere, and the reaction mixture was further treated according to Example 21 to obtain the compounds of formula (I).

The results are shown in Table 4.

(+)-4-hydroxy-4'-(1-propionyloxyethyl)biphenyl. $[\alpha]_D^{25} = +52°$ (c=1, CHCl$_3$), m.p.=133°-135° C.

EXAMPLE 32

The procedure of Example 24 for the acylation and succeeding treatments were followed except for use of 0.91 g (4 mmol) of (+)-4-benzyloxy-1-phenethyl alcohol and 0.49 g (4.8 mmol) of 2(s)-methylbutanoic acid to obtain 1.18 g (95% yield) of 2(s)-methylbutanoic ester of (+)-4-benzyloxy-1-phenethyl alcohol (II-32). $[\alpha]_D^{25} = +88°$ (c=1, CHCl$_3$), $n_D^{25} = 1.5326$.

0.94 g (3 mmol) of II-32, 15 ml of ethyl acetate and 0.3 g of 5% Pd-carbon were mixed and subjected to catalytic hydrogenation under normal pressure. The reaction mixture was further treated according to Example 21 to obtain 0.61 g (91.5% yield) of (+)-4-(1-2s-2-methylbutyryloxyethyl)phenol. $[\alpha]_D^{20} = +33.2°$ (c=1, CHCl$_3$), $n_D^{20} = 1.4976$.

EXAMPLE 33

13.5 g of the unreacted ester (acetic ester of (-)-4-benzyloxy-1-phenethyl alcohol) obtained in Example 1 was mixed with 100 ml of methanol and 30 g of 10% NaOH and reacted at 20° C. for 5 hours. The mixture was added with 50 ml of water and 200 ml of toluene and extracted therewith. The toluene layer was washed with water and concentrated under reduced pressure, and the residue was purified by silica gel column chromatography to obtain 11.1 g of (-)-4-benzyloxy-1-phenethyl alcohol (III-33).

1.14 g (5 mmol) of III-33 was dissolved in a mixed solution of 10 ml of pyridine and 10 ml of toluene, followed by dropwise addition of 0.74 g (5.5 mmol) of hexanoic acid chloride at 20° C. The mixture was kept at the same temperature for 2 hours and then at 40° C. for 3 hours. The reaction mixture was further treated and purified according to Example 21 to give 1.57 g (96.5% yield) of hexanoic ester of (-)-4-benzyloxy-1-phenethyl alcohol (II-33). $[\alpha]_D^{25} = -67°$ (c=1, CHCl$_3$), $n_D^{25} = 1.5281$.

By using 1.30 g (4 mmol) of II-33, the procedure of

TABLE 4

| Example No. | Acylating agent Compound name | Compound of formula (II) Yield | Compound of formula (II) Properties | Prouced compound of formula (I) R | Prouced compound of formula (I) 1 | Prouced compound of formula (I) Z | Prouced compound of formula (I) n | Prouced compound of formula (I) Yield | Prouced compound of formula (I) Properties |
|---|---|---|---|---|---|---|---|---|---|
| 28 | (2s, 3s)-2-chloro-3-methylpentanoic acid chloride | 94.5% | $n_D^{25}$ 1.5388 $[\alpha]_D^{25}$ +53° (c = 1, CHCl$_3$) | Cl CH$_3$ \| \| —CH—CH—C$_2$H$_5$ * * | 0 | H | 1 | 25% | $n_D^{25}$ 1.5216 $[\alpha]_D^{25}$ +60° (c = 1, CHCl$_3$) |
| 29 | 2s-2-chloro-propionic acid chloride | 95% | $n_D^{25}$ 1.5401 $[\alpha]_D^{25}$ = 60° (c = 1, CHCl$_3$) | Cl \| —CH—CH$_3$ * | 0 | H | 1 | 20% | $n_D^{25}$ 1.5238 $[\alpha]_D^{25}$ +68° (c = 1, CHCl$_3$) |
| 30 | Dodecanoic acid chloride | 92% | $n_D^{25}$ 1.5233 $[\alpha]_D^{25}$ +53° (c = 1, CHCl$_3$) | —(CH$_2$)$_{10}$CH$_3$ | 0 | H | 1 | 91% | $n_D^{25}$ 1.4901 $[\alpha]_D^{25}$ = 49° (c = 1, CHCl$_3$) |

EXAMPLE 31

The same acylation and succeeding treatments as conducted in Example 23 were followed except that 0.41 g (4.4 mmol) of propionic acid chloride was used in place of octanoic acid chloride to obtain 1.40 g (97.5% yield) of (+)-4-benzyloxy-4'-(1-propionyloxyethyl)-biphenyl (II-31). $[\alpha]_D^{25} = 55°$ (c=1, CHCl$_3$), m.p.=125° C.

By using 1.08 g (3 mmol) of II-31, the procedure of Example 22 was followed for the catalytic hydrogenation and succeeding treatments to obtain 0.86 g (91% yield) of (−)-4-(1-hexanoyloxyethyl)phenol. $[\alpha]_D^{25} = -73°$ (c=1, CHCl$_3$), $n_D^{25} = 1.5104$.

EXAMPLE 34

24.4 g (0.1 mol) of 2-fluoro-4-benzyloxyacetophenone and 300 ml of ethanol were supplied into a four-necked flask equipped with a stirrer and a thermometer. Then 3.8 g (0.1 mol) of sodium boron hydride was added at 15°-25° C. over a period of 10 minutes. The mixture was kept at the same temperature for 5 hours, then poured into ice-water and extracted with 500 ml of ethyl acetate. The organic layer was washed well with water and concentrated under reduced pressure to give 24.0 g of 2-fluoro-4-benzyloxy-1-phenethyl alcohol (VI-34).

19.7 g (0.08 mol) of VI-34 was dissolved in 200 ml of pyridine, followed by dropwise addition of 12.2 g of acetic anhydride at 30°–40° C., and the mixture was kept at 40°–50° C. for 6 hours. 400 ml of water was added to the reaction mixture. After separating the liquid phase, the organic layer was washed with a 2N hydrochloric acid solution, water, a 5% sodium bicarbonate solution and water in this order successively and then concentrated under reduced pressure to obtain 22.6 g (98% yield) of acetic ester of 2-fluoro-4-benzyloxy-1-phenethyl alcohol (V-34).

20 g (0.07 mol) of V-34 was mixed with 500 ml of 0.3M phosphate buffer (pH 7.0) and 3 g of Arthrobacterderived lipase and stirred vigorously at 38°–40° C. for a whole day and night. The reaction mixture was extracted with 500 ml of ethyl acetate. The organic layer was concentrated under reduced pressure and the residue was purified by column chromatography using a toluene/ethyl acetate mixed solution as developing solvent to obtain 8.32 g (48% yield) of (+)-2-fluoro-4-benzyloxy-1-phenethyl alcohol (III-34). $[\alpha]_D^{20} = 29.6°$ (c=1, CHCl$_3$), colorless oil.

Thereafter the same treatments as in Example 3 were conducted by using 3.69 g (0.015 mol) of III-34 instead of III-1 to obtain the compound of formula (I) shown in Table 5.

EXAMPLE 35

The procedure of Example 34 was followed except that 26.1 g (0.1 mol) of 2-chloro-4-benzyloxyacetophenone (VII-35) was used in place of 2-fluoro-4-benzyloxyacetophenone to obtain 7.9 g of (+)-2-chloro-4-benzyloxy-1-phenethyl alcohol (III-35). $[\alpha]_D^{20} = 33.2°$ (c=1, CHCl$_3$), $n_D^{20} = 1.5775$.

Thereafter the treatments of Example 3 were repeated by using 3.95 g (0.015 mol) of III-35 instead of III-1 to obtain the compound of formula (I) shown in Table 5.

EXAMPLE 36

According to the procedure of Example 3, except that (S)-2-fluoroheptyl tosylate was used in place of n-hexyl tosylate, alkylation and debenzylation were conducted and followed by after-treatment and purification to obtain (+)-4-(1'-(S)-2-fluoroheptyloxyethy)-phenol. $n_D^{20}$ 1.4951, $[\alpha]_D^{20} = +65.4°$ (c=1, CHCl$_3$).

EXAMPLE 37

The procedure of Example 14 was followed except that 6.5 g (0.0225 mol) of (S)-2-fluoroheptyl tosylate were used in place of n-hexyl tosylate. Alkylation and after-treatment were conducted to obtain 5.6 g of (+)-4-benzyloxy-4'-{1-(2(S)-fluoroheptyloxy)ethyl} biphenyl (VII-37). 4.2 g of the (VII-37) was debenzylated in accordance with the procedure of Example 14 to obtain 3.0 g of (+)-4-hydroxy-4'-{1-(2(S)-fluoroheptyloxy)ethyl}biphenyl (yield: 91%). $n_D^{20}$ 1.5383, $[\alpha]_D^{20} = +33.8°$ (c=1, CHCl$_3$).

EXAMPLE 38

1.85 g (0.0075 mol) of (+)-2-fluoro-4-benzyloxy-1-phenetyl alcohol (III-34) obtained in Example 34 were dissolved in 20 ml of pyridine, and then 1.07 g (0.01 mole) of butanoic acid chloride was added thereto and reacted at 40° C. for 2 hrs. After completion of the reaction, the reaction mixture was pour into water and then subjected to extraction treatment with 100 ml of toluene. The organic layer was washed with 2N-HCl, water, 5% aqueous sodium bicarbonate, and then water, in the order. The thus obtained organic layer was concentrated in vacuo to obtain 2.3 g of (+)-2-fluoro-4-benzyloxy-1-(1-acetoxyethyl)benzene (II-38). Yield: 98%.

1.58 g (0.005 mol) of the product (II-38) was dissolved into 20 ml of tetrahydrofuran, and then catalytic hydrogenation reaction was carried out adding 0.1 g of 5% Pd-C until the hydrogen consumption reached 100 ml. After completion of the reaction, the Pd-C catalyst was filtered and then the filtrate was concentrated in vacuo. The concentrated residue was purified through a silica gel column chromatography to obtain 0.64 g of 3-fluoro-4-(1-butanoyloxyethyl)phenol. (Yield: 82%). $[\alpha]_D^{20} = +60.1°$ (C=1.3, CHCl$_3$), $n_D^{20}$ 1.4913.

What is claimed is:

1. Optically active benzene derivatives represented by the formula (I):

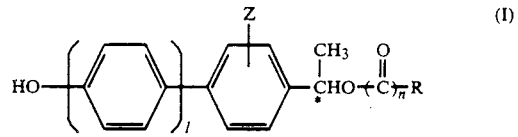

wherein R represents an alkyl or alkoxyalkyl group having 1 to 20 carbon atoms, which group may contain a halogen; Z represents a hydrogen atom or a halogen atom; l and n each represents a number of 0 or 1; and * indicates asymmetric carbon atom.

2. The optically active benzene derivatives according to claim 1, wherein when Z is a halogen atom and R is an alkyl group or an alkoxyalkyl group of 1–20 carbon atoms containing a halogen atom, the halogen atom is fluorine or chlorine atoms.

3. The optically active benzene derivatives according to claim 2, wherein R is a halogen-free alkyl group or alkoxyalkyl group having 1–20 carbon atoms.

4. The optically active benzene derivatives according to claim 3, wherein R represents an alkyl or alkoxyalkyl group having 1 to 20 carbon atoms and containing no halogen; and Z represents a hydrogen atom.

5. A process for preparing an optically active benzene derivative according to claim 1, which comprises

TABLE 5

| Example No. | Compound of formula (II) Yield | Compound of formula (II) Properties | Produced compound of formula (I) R | l | Z | n | Yield | Properties |
|---|---|---|---|---|---|---|---|---|
| 34 | 4.55 g (92%) | $[\alpha]_D^{20}$ +53.8° (c = 1, CHCl$_3$) $n_D^{20}$ 1.5162 | —C$_6$H$_{13}$ | O | F | O | 2.14 g (89%) | $[\alpha]_D^{20}$ +72.2° (c = 1, CHCl$_3$) $n_D^{20}$ 1.4708 |
| 35 | 4.73 g (91%) | $[\alpha]_D^{20}$ +51.3° (c = 1, CHCl$_3$) $n_D^{20}$ 1.5326 | —C$_6$H$_{13}$ | O | Cl | O | 2.23 g (87%) | $[\alpha]_D^{20}$ 75.3° (c = 1, CHCl$_3$) $n_D^{20}$ 1.4935 | debenzylating in the presence of hydrogen gas and a catalytic hydrogenation catalyst, an optically active benzyl derivative represented by the formula (II):

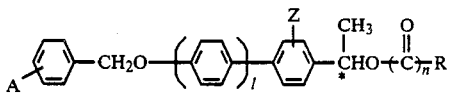
(II)

wherein R, Z, l, n and * have the same meanings as defined above, and A represents a hydrogen atom, a lower alkyl group, a lower alkoxy group or a halogen atom.

6. The process according to claim 5, wherein the catalytic hydrogenation catalyst is a palladium catalyst.

7. The process according to claim 5, wherein the amount of the catalytic hydrogenation catalyst used is 0.001 to 0.5 times by weight the amount of the optically active benzene derivative.

8. The process according to claim 5, comprising reacting an optical active alcohol represented by the formula (III):

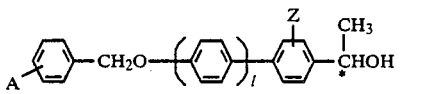
(III)

(wherein A, Z, l and * have the same meanings as defined above) with an alkylating or acylating agent represented by the formula (IV):

R—X (IV)

(wherein R is as defined above; and X represents a halogen atom, —OSO$_2$R" or —COY wherein R" represents a lower alkyl group or a phenyl group which may be substituted with a lower alkyl group, and Y represents a halogen atom, —OH or —OCOR) to produce an optically active benzyl derivative (II).

9. The process according to claim 8, using an alkylating agent to produce an optically active benzyl derivative of the formula (II) wherein n=0.

10. The process according to claim 9, wherein the alkylating agent is an alkyl or alkoxyalkyl halide having 1 to 20 carbon atoms, which halide may contain a halogen in the alkyl chain.

11. The process according to claim 10, wherein the alkyl halide or alkoxyalkyl halide of 1 to 20 carbon atoms, which may contain halogen in the alkyl chain, is an alkyl bromide, an alkyl iodide, an alkoxyalkyl bromide or alkoxyalkyl iodide.

12. The process according to claim 11 wherein the halogen of the alkyl halide or alkoxyalkyl halide having halogen in the alkyl chain of 1 to 20 carbon atoms is a fluorine atom or a chlorine atom.

13. The process according to claim 9, wherein the alkylating agent is an alkyl or an alkoxyalkyl ester of a lower alkylsulfonic acid, or an alkyl or an alkoxyalkyl ester of a benzenesulfonic acid, in which the benzene ring may be substituted with methyl group, the alkyl or alkoxyalkyl groups having 1 to 20 carbon atoms and being optionally substituted with halogen(s) in the alkyl chain.

14. The process according to claim 9, wherein the reaction is carried out in the presence of a basic substance.

15. The process according to claim 14, wherein the basic substance is an alkali metal hydride, an alkali metal hydroxide, an alkali earth metal hydroxide an alkali metal carbonate, an alkyl alkali metal, an alkali metal amide or metal alkoxide.

16. The process according to claim 14, wherein the amount of the basic substance used is 1 to 5 equivalents to one equivalent of the optical active alcohol (III).

17. The process according to claim 13, wherein the amount of the alkylating agent used is 1 to 5 equivalents to one equivalent of the optical active alcohol (III).

18. The process according to claim 8, wherein an acylating agent is used to produce an optically active benzyl derivative of the formula (II) wherein n=1.

19. The process according to claim 18, wherein the acylating agent is an aliphatic carboxylic acid having 1 to 20 carbon atoms, which may contain a halogen in the alkyl chain, or an acid anhydride or acid halide thereof.

20. The process according to claim 18, wherein the reaction is carried out in the presence of a catalyst.

21. The process according to claim 18, wherein the catalyst is an organic amine or an inorganic base.

22. The process according to claim 8, wherein the optical active alcohol (III) is produced by subjecting an ester of the formula (V):

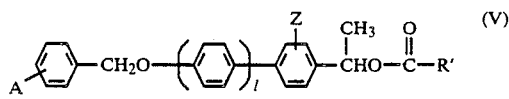
(V)

(wherein A, Z and l have the same meanings as defined above, and R' represents a lower alkyl group) to asymmetric hydrolysis by using an esterase having the ability to hydrolyze one of the enantiomers of said ester.

23. The process according to claim 22, wherein the reaction is carried out in a buffer solution.

24. The process according to claim 23, wherein the reaction is carried out in the presence of an organic solvent.

25. The process according to claim 22, using an esterase derived from a microorganism.

26. The process according to claim 25, wherein the microorganism is the one belonging to the genus Pseudomonas or Arthrobacter.

27. The process according to claim 22, wherein the reaction temperature is 10° C. to 60° C.

28. The process according to claim 22, wherein the ester (V) is produced by reacting an alcohol of the formula (VI):

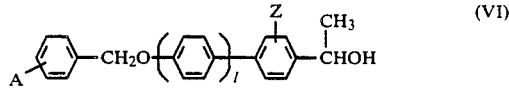
(VI)

(wherein A, Z and l are as defined above) with a lower alkylcarboxylic acid.

29. The process according to claim 28, wherein the lower alkylcarboxylic acid is an acid anhydride or acid halide of a lower alkylcarboxylic acid.

30. The process according to claim 28, wherein the reaction is carried out in the presence of a catalyst.

31. The process according to claim 30, wherein the catalyst is an organic amine or an inorganic basic substance.

32. The process according to claim 28, wherein the amount of the lower alkylcarboxylic acid used is 1 to 4 equivalents to one equivalent of the alcohol (VI).

33. The process according to claim 28, wherein the alcohol (VI) is produced by reducing a ketone of the formula (VII):

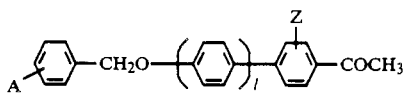

(wherein A, Z and l are as defined above) by using a reducing agent which is capable of reducing ketones into alcohols.

34. The process according to claim 33, wherein the reducing agent is sodium borohydride, lithium aluminum hydride, triisopropoxyaluminum, or borane.

35. The process according to claim 33, wherein the amount of the reducing agent used is 1 to 10 equivalents to one equivalent of the ketone (VII).

36. The process according to claim 33, wherein the reaction is carried out in the presence of an organic solvent.

37. The process according to claim 33, wherein the reaction temperature is −20° C. to 90° C.

38. An optically active benzyl derivative represented by the formula (II):

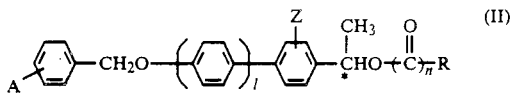

wherein A represents a hydrogen atom, a lower alkyl group, a lower alkoxyl group or a halogen atom; R represents an alkyl or alkoxyalkyl group having 1 to 20 carbon atoms, which group may contain a halogen; Z represents a hydrogen atom or a halogen atom; l and n each represents a number of 0 to 1; and * indicates asymmetric carbon atom.

39. An optically active alcohol represented by the formula (III):

wherein A represents a hydrogen atom, a lower alkyl group, a lower alkoxyl group or a halogen atom; Z represents a hydrogen atom or a halogen atom; l represents a number of 0 or 1; and * indicates asymmetric carbon atom.

* * * * *